United States Patent [19]

Marrelli

[11] Patent Number: 4,733,684
[45] Date of Patent: Mar. 29, 1988

[54] MEANS AND METHOD FOR TESTING THE HOMOGENEITY OF A SOLUTION

[75] Inventor: John D. Marrelli, Houston, Tex.

[73] Assignee: Texaco Inc., White Plains, N.Y.

[21] Appl. No.: 945,280

[22] Filed: Dec. 22, 1986

[51] Int. Cl.[4] .................. G01N 21/21; G01N 21/85
[52] U.S. Cl. .......................................... 137/2; 137/93; 137/115; 250/575; 356/367; 356/435
[58] Field of Search .................. 137/2, 93, 115; 356/435, 367; 250/225, 575

[56] References Cited

U.S. PATENT DOCUMENTS

| | | | |
|---|---|---|---|
| 1,746,525 | 2/1930 | Darrah | 137/93 |
| 3,309,308 | 3/1967 | Schad | 137/93 X |
| 3,489,906 | 1/1970 | Beer | 250/575 X |
| 3,605,775 | 9/1971 | Zaander et al. | 137/93 X |
| 3,724,957 | 4/1973 | Tamate et al. | 356/367 |
| 3,784,307 | 1/1974 | Jackson et al. | 250/575 X |
| 4,243,059 | 1/1981 | Hammon et al. | 137/2 |
| 4,448,534 | 5/1984 | Wertz et al. | 356/435 |
| 4,668,860 | 5/1987 | Anthon | 250/225 |

Primary Examiner—Martin P. Schwadron
Assistant Examiner—Stephen M. Hepperle
Attorney, Agent, or Firm—Robert A. Kulason; James J. O'Loughlin; Ronald G. Gillespie

[57] ABSTRACT

The system and the method of the present invention tests the homogeneity of a solution utilizing a housing which includes a first chamber for a reference solution and a second chamber for a test solution. The housing also includes a pair of transducers spatially related to the first and second chambers for providing signals in accordance with incident lights. The housing also includes a light source which provides light equally to both chambers in a manner so the light passes through the solutions in both chambers to be incident upon the transducers. Circuitry connected to the transducers provide an output signal related to the quality of the test solution in accordance with the signals provided by the transducers.

12 Claims, 5 Drawing Figures

POOR MIX

GOOD MIX

MEANS AND METHOD FOR TESTING THE HOMOGENEITY OF A SOLUTION

BACKGROUND OF THE INVENTION

Field of the Invention

The system and the method of the present invention relates to the testing of the homogeneity of solutions in general and, more particularly, to the optical testing of homogeneity.

SUMMARY OF THE INVENTION

The system and the method of the present invention tests the homogeneity of a solution utilizing a housing which includes a first chamber for a reference solution and a second chamber for a test solution. The housing also includes a pair of transducers spatially related to the first and second chambers for providing signals in accordance with incident lights. The housing also includes a light source which provides light equally to both chambers in a manner so the light passes through the solutions in both chambers to be incident upon the transducers. Circuitry connected to the transducers provide an output signal related to the quality of the test solution in accordance with the signals provided by the transducers.

The objects and advantages of the invention will appear more fully hereinafter, from a consideration of the detailed description which follows, taken together with the accompanying drawings wherin one embodiment is illustrated by way of example. It should be expressly understood, however, that the drawings are for illustration purposes only and are not to be construed as defining the limits of the invention.

DESCRIPTION OF THE INVENTION

Polyacrylamide is commonly used as a water viscosifying agent for Enhanced Oil Recovery projects in which mobility control is desired. A technical requirement for the use of some forms of polyacrylamide consists of grinding logs of solid polyacrylamide gel, dissolving this substance in field water such that it is well dispersed and no gel or high concentration micelles exist and finally injection under pressure of this mixture into an oil reservoir, via an injection well. Similar technical requirements of mixing also exist when liquid emulsions of polyacrylamide, kerosene and surfactant such as Nalco's Nalflo 555 are mixed with water.

If the mixing process is incomplete, plugging of the injection face of the well could occur. Field data indicates that undetected incomplete mixing has resulted in much higher injection pressures than desired. Since thousands of gallons of this mixture are injected and since polyacrylamide is known to be difficult to mix, many instances of poorly mixed injection solutions are observed in practice. One answer to the problem is to mix for a sufficient time to insure a homogeneous mixture, however it is difficult to predict this duration or to catch small lumps whose effects are small but cumulative. Operator observation of the injected fluid during the injection process is not practical as it is labor intensive and may also not result in catching lumps or "fish eyes" as inhomogeneous poorly mixed regions are called.

The present invention depends on the fact that poorly mixed solutions alter the transmission of light differently than well mixed solutions. The difference in optical transmission is characterized by an ensemble pattern recognition approach and it is this pattern difference which is detected.

Figure 1:
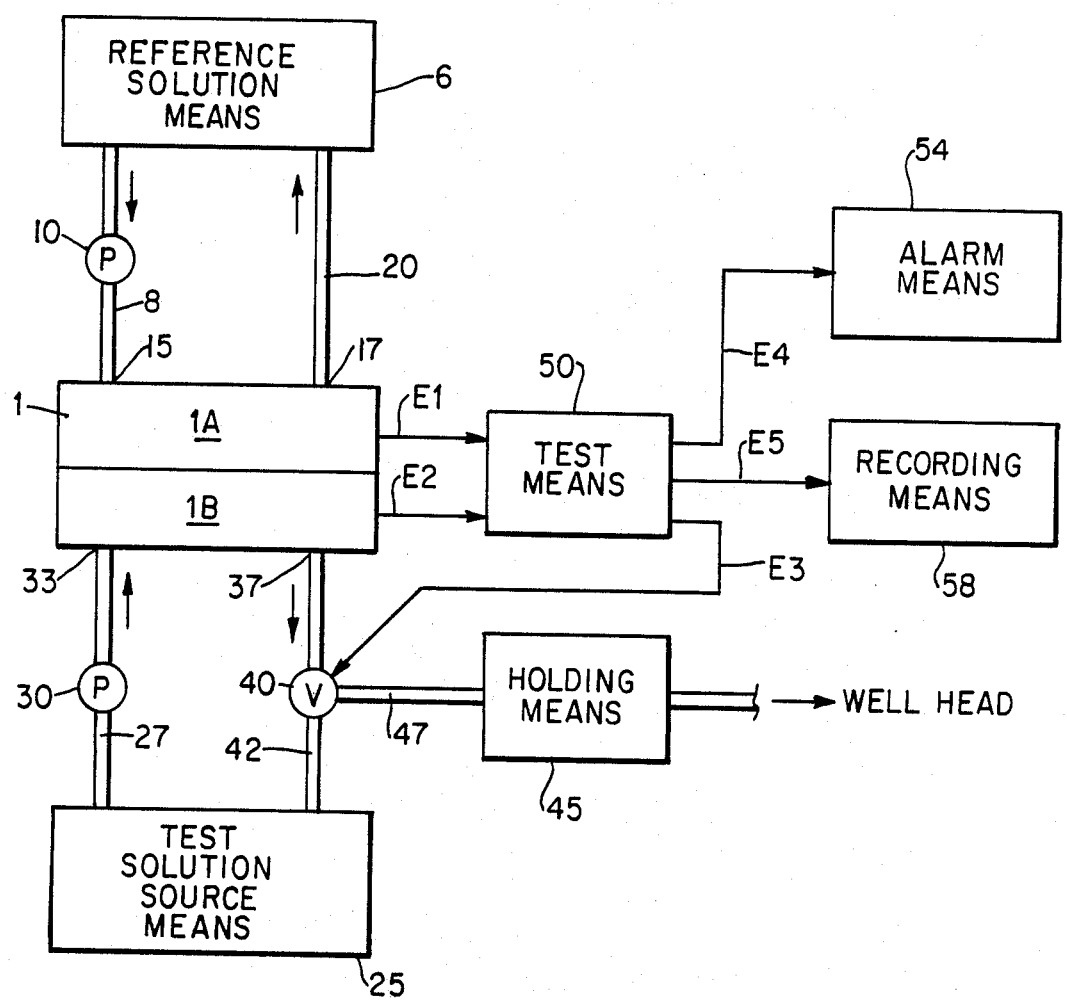
FIG. 1 is a simplified block diagram of a system constructed in accordance with the present invention to test the homogeneity of a solution.

Referring now to FIG. 1, a housing 1 is divided into two chambers 1A and 1B. The construction and operation of housing 1 will be discussed more fully hereinafter. A reference solution means 6 provides a thoroughly homogeneously mixed solution of the same type as is the solution to be tested, hereinafter referred to as the test solution, by way of a line 8 which is pumped by a pump 10. The reference solution enters chamber 1A through an entrance port 15 and exits chamber 1A of housing 1 by way of an exit port 17. The reference solution returns to reference solution means 6 by way of a line 20.

Similarly a test solution source means 25 provides the test solution through a line 27 utilizing a pump 30. The test solution enters chamber 1B of housing 1 by way of an entry port 33 and leaves chamber 1B through an exit port 37. The test solution is provided to an electrically operated two way valve 40 which can either provide the test solution back to test solution source means 25 via a line 42 for more mixing or if the test solution passes the test it is provided to holding means 45 by way of line 47. Holding means 45 provides the test solution to a well head when desired.

Housing 1 has a light source and provides light through chambers 1A and 1B, as hereinafter explained, in which the light passing through the reference solution and the test solution result in electrical signals E1 and E2 being provided to test means 50. Test means 50 will be described in greater detail later on. Suffice to say that test means 50 utilizes signal E1 and E2 to determine if the test solution is of the desired quality. Test means 50 provides a control signal E3 to valve 40. When the test solution is acceptable valve 40 is controlled to pass the test solution to holding means 45. When the test solution is not acceptable, signal E3 causes valve 40 to return the test solution to test solution source means 25 for further mixing. Test means 50 provides another signal E4 to alarm means 54. Alarm means 54 may include audio or visual alarms or both. When the test results are unacceptable, signal E4 causes the alarms of alarm means 54 to be activated. Test means 50 provides a signal E5 to recorder means 58 for recording the results of the test. Recorder means 58 may be a strip chart recorder or may be any other type of recording device.

Figure 2:
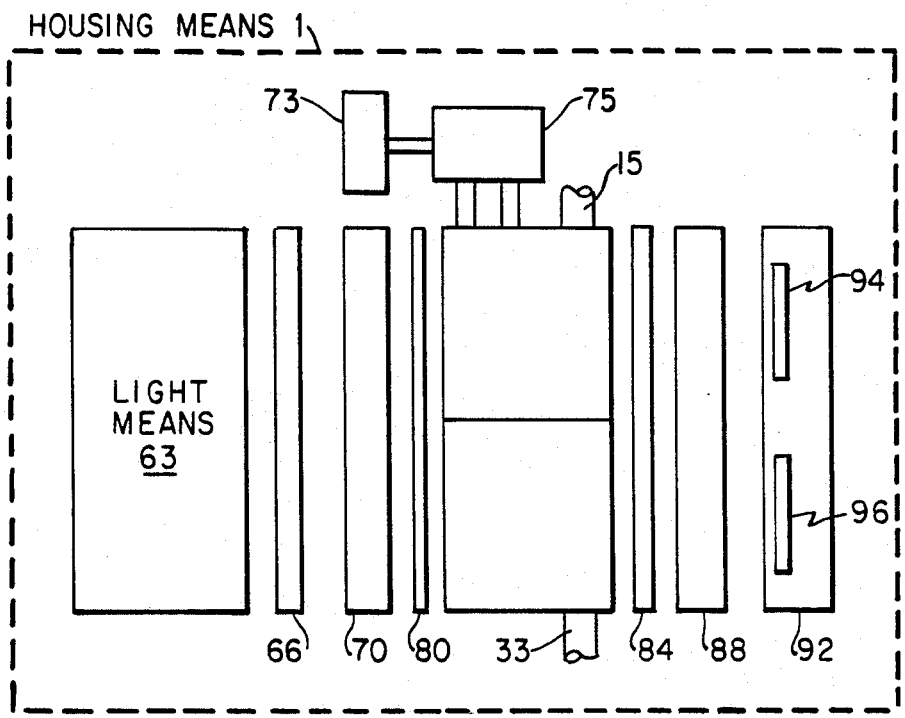
FIG. 2 is a simplified schematic type drawing of the housing means shown in FIG. 1.

Referring now to FIG. 2, housing 1 includes light means 63, which may be a conventional light source, providing light to a defusing filter 66. Defusing filter 66 permits one to use an inexpensive light source, which essentially provides a point of light, and assure the equal distribution of light intensity over the entire field so as not to develop regional errors. The defused light is provided to a movable polarizer 70. Polarizer 70 may be of the type sold by Ray Enterprises Inc. under their part number 241661701. Polarizer 70 is mounted on and supported by an axle (not shown) which passes through housing 1. The external edge of polarizer 70 has teeth so that polarizer 70 may be rotated around the axle (not shown) by a drive gear 73 rotated by a motor 75. The reason for rotating polarizer 70 will be explained hereinafter.

Positioned between chambers 1A and 1B and polarizer 70 is an optically clear barrier 80 which may be purchased from Ray Enterprises Inc., as their part number 241665827. Light passing through polarizer 70 and barrier 80 enters chambers 1A and 1B through which the solutions are flowing as previously explained. The light passing through chambers 1A and 1B passes through another optically clear barrier 84 and thence through a stationary polarizer 88. Polarizer 88 may be the same type of polarizer as polarizer 70. A light tight cover means 92 has photoelectric cells 94 and 96 mounted on it which provide signals E1 and E2, respectively in accordance with the light incident upon them.

Figure 3:
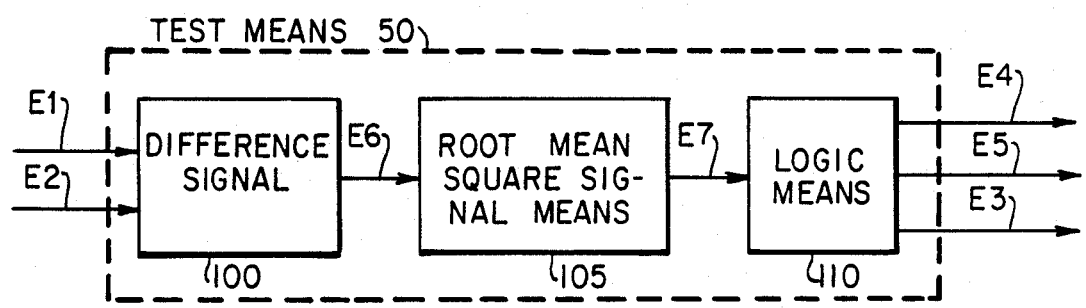
FIG. 3 is a simplified block diagram of the test means shown in FIG. 1.

Referring now to FIG. 3, test means 50 includes a difference signal means 100 receiving signals E1, E2 and provides a signal E6 corresponding to the difference between signals E1 and E2. Difference signal means 100 may be a differential operational amplifier with associated circuitry. Signal E6 is provided to a root mean square signal means 105 which in turn provides a signal E7 representative of the root mean square of signal E6. Signal E7 is provided to logic means 110 which utilizes signal E7 to provide signals E3, E4 and E5. It should be noted that logic means 110 is not novel in itself and the details of which are not needed to understand the present invention. Suffice to say that logic means 110 would include circuitry to provide signals E3 and E4 when signal E7 exceeds certain predetermined criteria. Signal E5 would be provided in accordance with signal E7 so that a record of the test may be made.

In operation, reference solution means 6 and test solution source means 25 simultaneously provide their solutions to chamber 1A and 1B, respectively, of housing 1. Light means 63 provides light which is diffused by diffusing element 66. The diffused light is provided to rotating polarizer 70. Whenever polarizer 70 and polarizer 80 are in phase with each other there will be full light transmission from light means 63 through chambers 1A, 1B to cells 94 and 96, respectively, except for the attenuation of the light by the solutions in chambers 1A and 1B. Whenever polarizers 70, 88 are at right angles to each other, that is 90 degrees out of phase with each other, light will pass through chambers 1A and 1B. However, due to the polarization effects of polarizers 70 and 88 being out of phase, substantially no light will reach photo cells 94 and 96. Thus it can be seen that during each revolution of polarizer 70 the intensity of light passing through chambers 1A and 1B and incident upon photo cells 94 and 96, respectively, will be sinusoidal in form. Accordingly, signals E1 and E2 will have peaks of one polarity when polarizers 70 and 88 are in phase and peaks of another polarity when polarizers 70 and 80 are 90 degrees out of phase. For every complete revolution of polarizer 70 there will be four peaks to each signal E1 or E2.

Figure 4A:
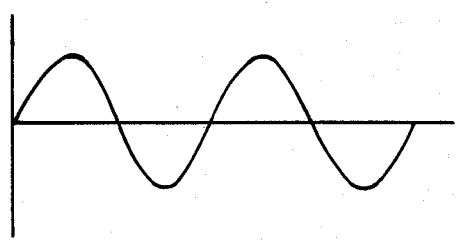
FIGS. 4A and 4B are diagrammatic representations of signal E6 for a poor homogeneousness of a test solution and for a good homogeneousness of a test solution, respectively.
Figure 4B:
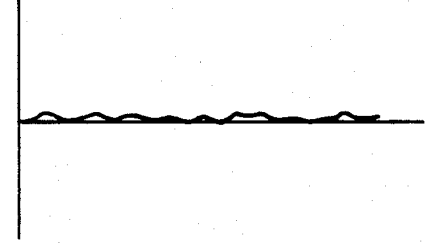

With reference to FIGS. 4A and 4B, FIG. 4A shows signal E6 when there has been poor mixing of the test solution. As a result the difference between signals E1 and E2 is great and shows up as a large peak-to-peak swing of signal E6. On the other hand, when there is good mixing of the test solution, the difference between signals E1 and E2 is small and signal E6 would appear similar to that what is shown in FIG. 4B.

Although the present invention has heretofore been described in a testing of polyacrylamide in a solution used in an enhanced oil recovery project, it may also be utilized to test for poorly mixed solutions of polysaccharides, such as Xanthan, or any other type of solution in other industrial fields.

What is claimed is:

1. A system for testing the homogeneity of a solution comprising:
    means for providing a test solution;
    means for providing a reference solution;
    housing means including:
    first chamber means for receiving the reference solution,
    second chamber means for receiving the test solution,
    first signal means spatially related to the first chamber means for providing a first signal in accordance with incident light,
    second signal means spatially related to the second chamber means for providing a second signal in accordance with incident light, and
    light means for providing light equally to both chamber means in a manner so that the light passes through the solution in both chamber means to be incident upon the first and second signal means, and
    polarizing means located in the housing means for polarizing the light from the light means prior to the light being incident on the first and second signal means,
    said polarizing means includes a rotatable polarizing filter means for polarizing the light, and
    a fixed polarizing filter means for polarizing light, and said rotatable polarizing filter means and said fixed polarizing filter means being spatially arranged with both chamber means so that both chamber means are between the two polarizing filter means, and
    further comprising means for rotating the rotatable polarizing filter means; and
    output means connected to both signal means for providing an output signal related to the quality of the test solution in accordance with the first and second signals from the first and second signal means, respectively.

2. A system as described in claim 1 in which the light means includes:
    a source means for providing light, and
    diffusing means spatially arranged between the light source and one of the polarizing filter means for diffusing the light from the source means so that light provided to both chamber means is provided equally.

3. A system as described in claim 2 in which the output means includes:
    difference means connected to the first and second signal means for providing a signal corresponding to the difference between the first signal and the second signal, and
    third signal means connected to the difference means for providing a signal as the output signal in accordance with the root means square of the signal from the difference means.

4. A method for testing the homogeneity of a solution comprising the steps of:
   providing a test solution,
   providing a reference solution,
   receiving the reference solution in a first chamber of a housing,
   receiving the test solution in a second chamber of the housing,
   providing a first signal with a first signal means spatially related to the first chamber in accordance with incident light on the first signal means,
   providing a second signal with a second signal means spatially related to the second chamber in accordance with incident light on the second signal means,
   providing light equally to both chambers in a manner so that the light passes through the solutions in both chambers to be incident upon the first and second signal means,
   polarizing the light from the light means prior to the light being incident on the first and second signal means,
   said polarizing step including:
   polarizing the light with a rotatable polarizing filter, and
   polarizing the light with a fixed polarizing filter,
   arranging the rotatable polarizing filter and the fixed polarizing filter with both chambers so that both chambers are between the two polarizing filters; and
   further comprising the step of rotating the rotatable polarizing filter,
   providing an output signal related to the quality of the test solution in accordance with the first and second signals.

5. A method as described in claim 4 in which the light step includes:
   providing light with a light source, and
   diffusing the light from the light source so as to provide light to both chambers equally.

6. A method as described in claim 5 in which the output step includes:
   providing a difference signal corresponding to the difference between the first signal and the second signal, and
   providing a signal as the output signal in accordance with the root means square of the difference signal.

7. A system controlling the application of a solution to a well comprising:
   solution means for providing a solution;
   reference means for providing a reference solution;
   housing means including:
   first chamber means for receiving the reference solution and for returning the reference solution to the reference means,
   second chamber means for receiving the solution and providing the solution,
   first signal means spatially related to the first chamber means for providing a first signal in accordance with incident light,
   second signal means spatially related to the second chamber means for providing a second signal in accordance with incident light,
   light means for providing light equally to both chamber means in a manner so that the light passes through the solutions in both chamber means to be incident upon the first and second signal means, and
   polarizing means located in the housing means for polarizing the light from the light means prior to the light being incident on the first and second signal means,
   said polarizing means includes:
   a rotatable polarizing filter means for polarizing the light, and
   a fixed polarizing filter means for polarizing light, and said rotatable polarizing filter means and said fixed polarizing filter means being spatially arranged with both chamber means so that both chamber means are between the two polarizing filter means, and
   further comprising means for rotating the rotatable polarizing filter means; and
   control means connected to the well, to the solution means and to the second chamber means for providing the solution from the second chamber means either to the well or to the solution means in accordance with a control signal; and
   control signal means connected to both signal means and to the control means for providing the control signal to the control means in accordance with the first and second signals from the first and second signal means, respectively.

8. A system as described in claim 7 in which the light means includes:
   a source means for providing light, and
   diffusing means spatially arranged between the light source and one of the polarizing filter means for diffusing the light from the source means so as to provide light to both chamber means equally.

9. A system as described in claim 8 in which the control signal means includes:
   difference means connected to the first and second signal means for providing a difference signal corresponding to the difference between the first signal and the second signal, and
   third signal means connected to the difference means for providing a signal as the control signal in accordance with the root means square of the difference signal from the difference means.

10. A method controlling the application of a solution to a well comprising the steps of:
    providing a solution from a source;
    providing a reference solution;
    receiving the reference solution in a first chamber;
    returning the reference solution from the first chamber to the reference means;
    means for receiving the solution in a second chamber, providing the solution from the second chamber;
    providing a first signal in accordance with incident light, on a first signal means spatially related to the first chamber;
    providing a second signal in accordance with incident light, on a second signal means spatially related to the second chamber;
    providing light equally to both chambers in a manner so that the light passes through the solutions in both chambers to be incident upon the first and second signal means;
    polarizing the light prior to the light being incident on the first and second signal means,
    said polarizing step includes:
    polarizing the light with a rotatable polarizing filter, and
    polarizing the light with a fixed polarizing filter and said rotatable polarizing filter and said fixed polarizing filter being spatially arranged with both chambers so that both chambers are between the two polarizing filters, and further comprising the step of rotating the rotatable polarizing filter;

using control means connected to the well, to the solution means and to the second chamber means to provide the solution from the second chamber either to the well or to the solution source in accordance with a control signal, and providing the control signal to the control means in accordance with the first and second signals from the first and second signal means, respectively.

11. A method as described in claim 10 in which the light step includes:

providing light with a source, and diffusing the light from the source so as to provide light to both chambers equally.

12. A method as described in claim 11 in which the control signal step includes:

providing a difference signal corresponding to the difference between the first signal and the second signal, and providing a signal as the control signal in accordance with the root means square of the difference signal.

* * * * *